United States Patent

Archambault

[11] Patent Number: 5,762,494
[45] Date of Patent: Jun. 9, 1998

[54] APPLICATOR DEVICE AND METHOD

[76] Inventor: Gregory A. Archambault, 1414 Kingsley Ave., Orange Park, Fla. 32073

[21] Appl. No.: 822,804

[22] Filed: Mar. 24, 1997

[51] Int. Cl.$^6$ .................................................. A61G 17/02
[52] U.S. Cl. .................... 433/80; 433/229; 604/1; 424/435
[58] Field of Search ..................... 433/80, 215, 229; 604/1; 424/435

[56] References Cited

U.S. PATENT DOCUMENTS

| | | | |
|---|---|---|---|
| 307,537 | 11/1884 | Foulks | 433/215 |
| 1,111,679 | 9/1914 | Silbaugh | 604/307 |
| 1,622,616 | 3/1927 | Temple | 433/215 |
| 2,510,490 | 6/1950 | Ager | 433/80 |
| 3,352,307 | 11/1967 | Bloxham | 604/1 |
| 3,814,095 | 6/1974 | Lubens | 604/307 |
| 4,020,558 | 5/1977 | Cournut et al. | 433/80 |
| 4,192,300 | 3/1980 | Devers | 604/1 |
| 4,457,756 | 7/1984 | Kern et al. | 604/1 |
| 5,122,127 | 6/1992 | Stanley | 424/435 |
| 5,288,498 | 2/1994 | Stanley et al. | 424/435 |

*Primary Examiner*—John J. Wilson
*Attorney, Agent, or Firm*—Thomas C. Saitta

[57] ABSTRACT

A mucosal applicator for topical anesthetics comprising a delivery member for retaining and delivering the anesthetic to the mucosal tissue, an adhesive which adheres the delivery member to the tissue, and a retention member connected to the delivery member which provides a biasing force against the delivery member to further secure the delivery member in position when the device is inserted into the patient's mouth.

17 Claims, 2 Drawing Sheets

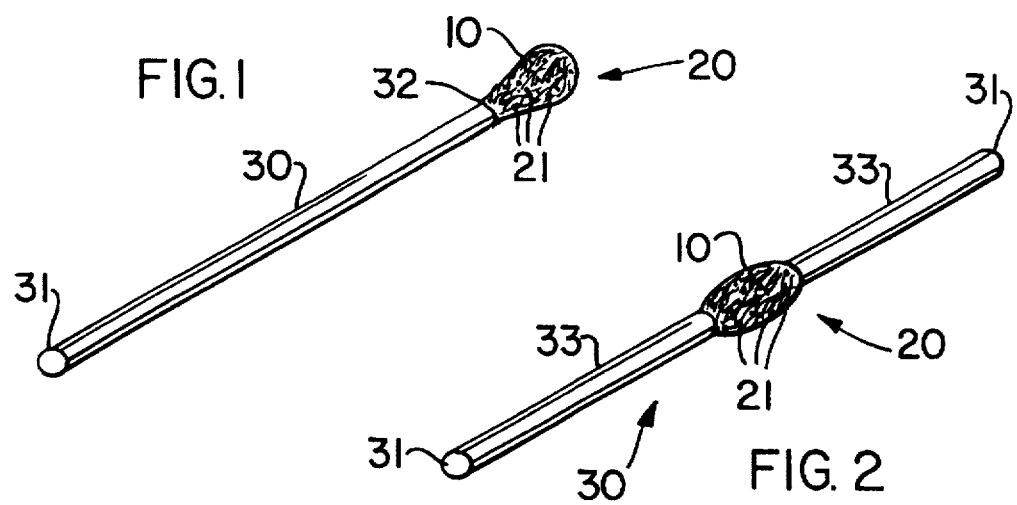
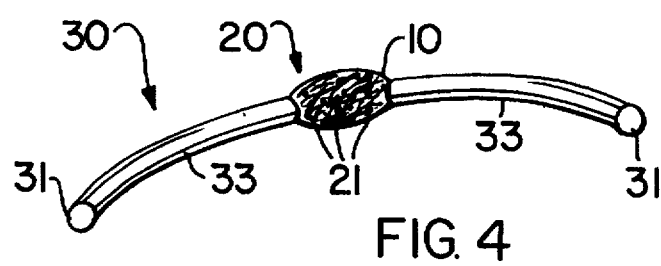
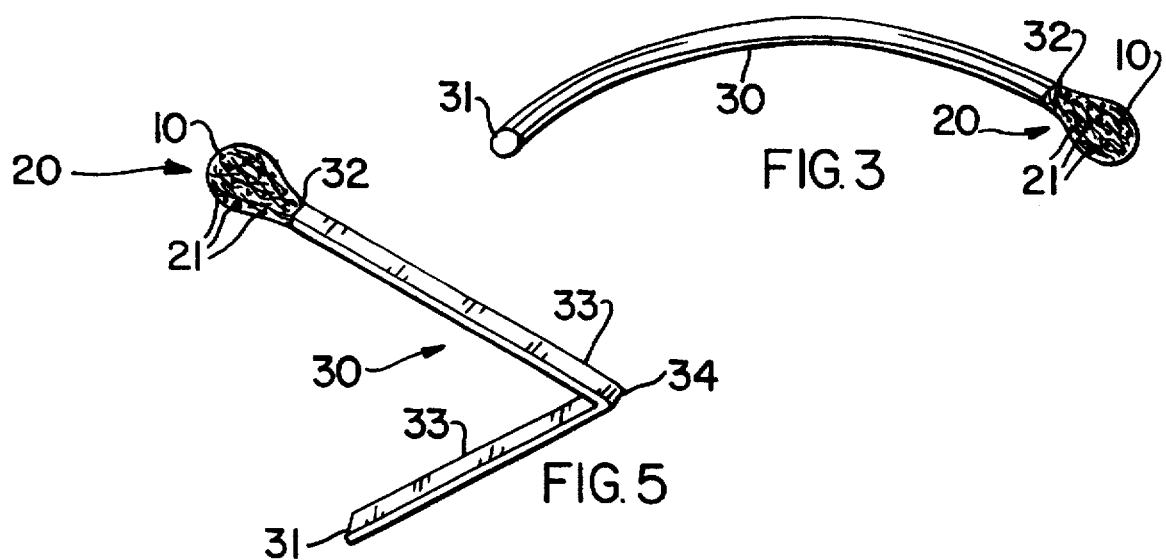

APPLICATOR DEVICE AND METHOD

BACKGROUND OF THE INVENTION

This invention relates generally to the field of topical anesthetic applicator devices, and more particularly to such devices used in the field of dentistry for application of topical anesthetic to the oral tissue within the mouth and particularly to the alveolar mucosa.

Topical anesthetics are well known means to anesthetize a small region of skin or tissue. In the dental field, topical anesthetics are used to anesthetize a region of oral or mucosal tissue prior to performing certain dental procedures, such as scaling, root planing, polishing, probing, needle injection for nerve blockage, restorative bonding, suture removal, gingival curettage, tissue grafting, application of antibiotic fibers into periodontal pockets or soft tissue biopsy procedures. Of these procedures, the use of topical anesthetic to reduce or eliminate the pain resulting from insertion of a needle through the alveolar mucosa for injection of anesthetic is probably the most common. The typical technique involves the use of anesthetic supplied in liquid or gel form. The dentist dips a cotton or foam swab into the anesthetic container and then transfers the anesthetic to desired area of the patient's mouth. To avoid contamination of the anesthetic supply, liquid anesthetic may be drawn into small syringes and then deposited onto the applicator swab. Obvious problems with the known methodologies, beyond the contamination issue, are that the anesthetic may be accidentally applied to non-essential regions, successive applications may be required to sufficiently anesthetize the region, and there is no way to secure or retain the swab at the desired location for any length of time.

Dental techniques and devices have been developed to address some of these problems. For example, the use of dosed applicator swabs with pre-measured amounts of anesthetic provide a means to control the amount of anesthetic delivered to the mucosal tissue but this does not solve the problem of securing the swab to the tissue for an extended period of time. With a swab properly positioned in the mouth, it is very difficult for the patient not to accidentally or intentionally because of discomfort move or adjust the swab by movement of the jaw or tongue. This is especially true of children, which is the class of patient most in need of local anesthetic delivered topically and painlessly prior to a pain inducing dental procedure. To address this problem, devices known as transmucosal patches, similar to the well known transdermal patches, have been produced as a means to deliver topical anesthetic to oral tissue. The transmucosal patch, such as produced by Noven Pharmaceuticals, Inc. and sold under the brand name DENTIPATCH, comprises an anesthetic such as lidocaine incorporated in an adhesive matrix which is applied directly to the oral tissue. The adhesive acts to retain the patch at the desired location. The dentist secures the patch by pressing it firmly in place and smoothing it for a period of 20 to 60 seconds, and is usually required to leave the patch in place for 2.5 to 15 minutes. Problems with this device include the lack of rigid support means to enable easy placement and pressure application to adhere the patch to the oral tissue, the fact that the patch, due to its small size, can be easily shifted by the patient's tongue, and the fact that the adhesive will not properly adhere if the oral tissue is too moist when the patch is applied, if the patch is applied in a location adjacent a salivary duct, or if the anatomical location of the desired position does not provide a generally planar contact surface. In particular, the optimum location for application of topical application is often the alveolar mucosa, the region of thin, soft tissue at the curved juncture forming the interior base of the cheek or lip, and the patch does not adhere well in this region because of the curved structure and the elasticity of the mucosa tissue.

It is an object of this invention to provide a device for the delivery of topical anesthetic to oral tissue which alleviates the problems set forth above with regard to the known techniques and applicator devices. It is a further object to provide such a device with an anesthetic delivery member, such as a cotton swab, polymer foam or gel-like matrix for receiving and dispersing an anesthetic, which is pre-dosed with a precise amount of anesthetic for controlled delivery of the proper amount of anesthetic to the patient. It is a further object to provide such a device which further comprises a first retention means for securing the anesthetic delivery member at the desired location, especially in the alveolar mucosa region, the first retention means being an adhesive suitable for use in the moist environment of the mouth, and a second retention means for securing the anesthetic delivery member at the desired location, the second retention means being a relatively rigid support member to assist in the proper placement of the anesthetic delivery member within the mouth and also to provide a mechanical biasing force which applies pressure to the anesthetic delivery member to insure correct contact to the mucosal tissue for proper delivery of the anesthetic and to prevent accidental or intentional movement of the anesthetic delivery member by the patient.

SUMMARY OF THE INVENTION

The invention is a device for transmucosal delivery of topical anesthetic, primarily to the mucosal tissue region of the mouth. The device comprises in general an anesthetic delivery member having a first retention means and a second retention means for properly securing the delivery member in position to prevent accidental or intentional shifting of the delivery member by the patient. The delivery member may comprise an absorbent swab or patch of spun cotton fibers or the like, a polymer foam body, or a polymer or gel matrix of material capable of retaining and releasing an anesthetic suitable for use in the mouth, such as lidocaine. The delivery member is preferably pre-dosed with an exact measured amount of anesthetic. The first retention means comprises an adhesive suitable for use in the moist environment of the mouth. The first retention means is preferably incorporated directly into the material composing the delivery member, and may be an inherent property of the material composing the delivery member, may be applied or affixed to the exterior of the delivery member as a separate backing layer extending beyond the periphery of the delivery member to create a perimeter region of adhesion, or may be applied to the contact side of the delivery member provided it is permeable to the anesthetic.

The second retention means is a relatively rigid member capable of mechanically securing the delivery member in proper position through interaction with particular anatomical structures of the mouth, including the cheek, lips and teeth. The second retention means preferably provides a biasing force against the delivery member resulting from the structural configuration of the second retention means in conjunction with limiting anatomical structures of the mouth. The second retention means is preferably formed of a relatively rigid but flexible material, such as a generally thin rod, tube or flat bar of material having suitable properties for use in the mouth, such as plastic, metal, wire, wood or processed paper, to which is attached by suitable known means the anesthetic delivery member. The second retention member can be straight, curved, angularly jointed, or a combination of these structures in any configuration which provides a force bias when the straight or curved members, or the segments forming the angular joint, are compressed. The second retention member may be configured prior to use or may be formed of a slightly malleable material which allows a particular configuration to be imparted by the dentist, the malleable material retaining enough memory to create the biasing force. The delivery means may be attached on an end of the second retention member or at a point between the ends.

The device is used by positioning the anesthetic delivery member at the desired location of the mucosa. The first retention means adhesively secures the delivery member in contact with the oral tissue to allow proper transfer of the anesthetic. The particular configuration of the second retention means is chosen with regard to the region of the mouth where the delivery means is to be temporarily affixed. If the anesthetic is to be delivered at the mucosal base of the back teeth, then the second retention means will be retained by the combination of the interior of the cheek, the mucosa region, the alveolar bone region and/or the teeth themselves. If the anesthetic is to be delivered at the mucosal base of the front teeth, then the secondary retention means will be retained by the combination of the interior of the lip, the mucosa region, the alveolar bone region and/or the teeth themselves. The biasing force created by the compressive forces acting on the second retention means further secures the delivery member in proper position. The second retention means being a relatively rigid structural material, its presence in the mouth also serves as a reminder which inhibits the patient from intentionally shifting or manipulating the delivery member.

BRIEF DESCRIPTION OF THE DRAWINGS

FIG. 1 is a perspective view of the invention showing a straight second retention means with the anesthetic delivery member affixed to an attached end.

FIG. 2 is a perspective view of an alternative embodiment of the invention showing a straight second retention means where the anesthetic delivery means is affixed between the free ends.

FIG. 3 is a perspective view of an alternative embodiment of the invention showing a curved second retention means with the anesthetic delivery member affixed to an attached end.

FIG. 4 is a perspective view of an alternative embodiment of the invention showing a curved second retention means where the anesthetic delivery means is affixed between the free ends.

FIG. 5 is a perspective view of an alternative embodiment of the invention showing a jointed second retention means for use in the back of the mouth.

DETAILED DESCRIPTION OF THE INVENTION

Figure 6:
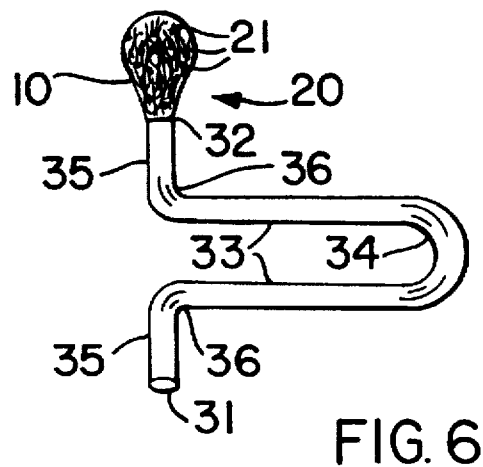
FIG. 6 is a perspective view of an alternative embodiment of the invention showing a jointed second retention means for use in the front of the mouth.

With reference to the drawings, the invention will now be described in detail with regard to the preferred embodiment and best mode. The invention is an applicator for transmucosal application of topical anesthetic, or other medical or therapeutic liquid substance, to the mucosal tissues in the mouth, and in particular to the mucosal region between the base of the alveolar bone region and the inside of the cheek or lip, and comprises in general an anesthetic delivery member 10 and first and second retention means 20 and 30 for retaining or securing the delivery member 10 at the desired location on the alveolar mucosa for the necessary period of time, typically 2.5 to 15 minutes, required to deliver sufficient anesthetic into and through the tissues to desensitize the area, thus allowing successive dental procedures to be performed without pain. Primarily, the invention is intended to be used where anesthetic is to be injected adjacent the periosteum at the base of a tooth in order for it to diffuse through and reach the nerves in the most efficient manner, which is accomplished by passing a needle through the mucosa.

The anesthetic delivery member 10 is a member formed of material which can retain and deliver an amount of anesthetic suitable for use in the mouth, such as lidocaine. Preferably the delivery member 10 is pre-dosed with a measured amount of anesthetic and packaged in suitable material to create a relatively long shelf life, the package being opened at the time of use, but the device could also be used where the anesthetic is applied to the delivery member 10 from a common container or source. The delivery member 10 may be composed of any suitable material capable of retaining and delivering the anesthetic and of being fixedly attached to a second retention means 30, such as spun or woven cotton or other natural or synthetic fibers, polymer or natural foam or sponge material, or polymer-based gels or matrices. The delivery member 10 may be shaped in various configurations such as round, oval, square or rectangular, and can be spheroid or relatively flat. Preferably the delivery member 10 is generally round or ovoid to better match the curve of the alveolar mucosa area. Such delivery members 10 are well known in the art.

A first retention means 20 is combined with the anesthetic delivery member 10, the first retention means 20 being a means to adhesively secure the delivery member 10 to the mucosal tissue. The first retention means 20 may be an inherent property of the material forming the delivery member 10, such as where an adhesive polymer or gel is used to form the body of the delivery member 10. The first retention means 20 is composed of any adhesive suitable for use in the moist environment of the mouth and which provides for generally secure but relatively easily removable adhesion to the tissue. Preferably, the first retention means 20 is an adhesive component 21 incorporated into the bulk or matrix of the delivery member 10 or existing as a inherent property of the delivery member 10, as shown in FIGS. 1 through 7, but the first retention means 20 may be affixed as an adhesive backing film 23 which extends beyond the periphery of the back or non-contact side of the delivery member 10 to create an adhesive peripheral flange, as shown in FIG. 8. Alternatively, the first retention means 20 may be applied directly onto the contact side of the delivery member 10 as a separate adhesive layer 22, as shown in FIG. 9, provided the layer 22 is permeable to the anesthetic.

Figure 7:
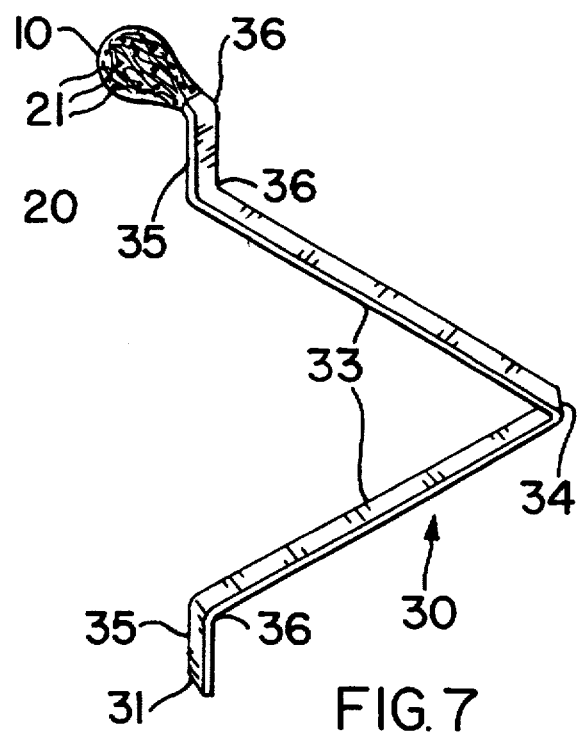
FIG. 7 is a perspective view of an alternative embodiment of the invention showing a more angularly jointed second retention means.
Figure 8:
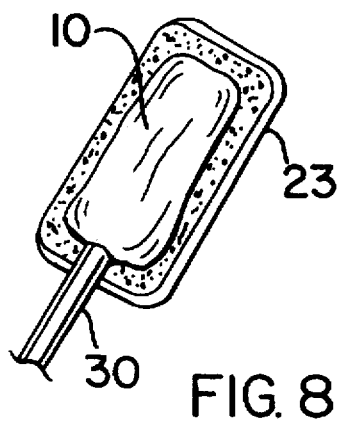
FIG. 8 is a partial view of an alternative embodiment of the invention showing an adhesive backing film attached to the anesthetic delivery member.
Figure 9:
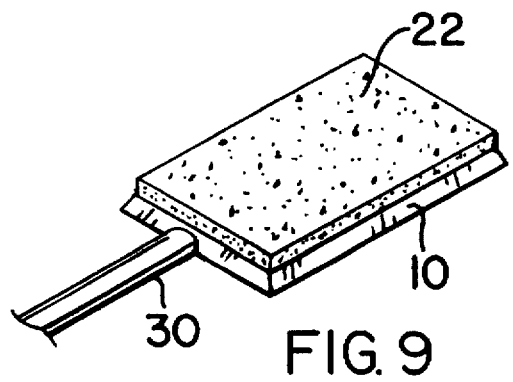
FIG. 9 is a partial view of an alternative embodiment of the invention showing an adhesive layer adhered to the front of the anesthetic delivery member.

The delivery member 10 is securely attached to a second retention member 30 which is composed of a generally rigid but flexible material, such as plastic, metal, wood or processed paper, and has a main body preferably shaped as a generally elongated, thin, rod or tube, as shown in FIGS. 1 through 4, 6, 8 and 9, or as a generally thin, flat bar as shown in the FIGS. 5 and 7. The second retention means 30 is simultaneously sufficiently rigid and flexible as to allow a compressive force to be applied against it which results in a biasing force opposite to the compressive force seeking to return the second retention means 30 to its non-compressed configuration, in the manner of a leaf spring. The second retention means 30 may be preformed with the desired configuration or it may be composed of a generally malleable material, such as plastic or metal, which can be bent by the dentist into the desired configuration, the malleable material retaining enough memory such that a biasing force is inherent even after the material has been shaped into the desired configuration. The second retention means 30 applies this biasing force against the delivery member 10 after the delivery member 10 has been properly positioned on the mucosa, the second retention means 30 being manually compressed by the dentist for insertion and positioning of the device into the mouth. The second retention means 30 is properly positioned and aligned relative to one or more anatomical features of the patient's mouth, such as the interior of the cheek or lip, the alveolar mucosal region, the alveolar bone region or the teeth themselves, so that the anatomical features act as the expansion limiting detent or stop which prevents the second retention means 30 from rebounding fully to its noncompressed configuration, thus sustaining a biasing force which secures the delivery member 10 in conjunction with and in addition to the adhesive first retention means 20. In this manner, if the adhesion of the first retention member 20 is compromised by excessive moisture or other factors, the second retention member 30 will retain the delivery member 10 in the proper position. The biasing force of the second retention member 30 insures that the delivery member 10 will remain in contact with the mucosal tissue for optimum delivery of the anesthetic. Additionally, because the second retention member 30 is a mechanical or structural member with rigidity and inherent biasing force, the patient will be aware that the structure is in place because the device itself as well as pressure from the biasing force of the device will be felt in the patient's mouth, and the patient will be less likely to accidentally or intentionally move the delivery member 10.

The second retention means 30 may have a number of configurations, and the delivery member 10 may be attached to the second retention means 30 at different locations, as shown in FIGS. 1 through 7. In FIG. 1, the most basic embodiment of the invention is shown, where the delivery member 10 incorporates first retention means 20 as an impregnated adhesive 21 and is attached to the attached end 32 of the second retention means 30, an elongated thin rod with a free end 31. To position this embodiment of the device, the delivery member 10 is set into the curve of the alveolar mucosa and pressed against the tissue to adhere it in place, and the second retention means 30 is positioned generally vertically inside the mouth to provide a downward or upward biasing force against the delivery member 10. In FIG. 2, a variation on the straight-bodied second retention means 30 is shown, where the delivery member 10 is attached at some point between the two free ends 31, forming two body segments 33. To properly position this embodiment of the device, the delivery member 10 is adhered to the desired location and the second retention means 30 aligned along the trough formed between the alveolar mucosa and the interior of the cheek. The natural curve of this trough biases the second retention member 30 to secure it in a stable manner. In similar manner, the device may be configured as in FIGS. 3 and 4, where the secondary retention means 30 is pre-formed curved rather than straight.

The more preferred embodiments are shown in FIGS. 5, 6 and 7, where the second retention member 30 is configured with a pre-formed flexed body joint 34. As before, the second retention means 30 may be round in cross-section, as seen in FIG. 6, or may be rectangular in cross-section, as seen in FIGS. 5 and 7. The device in FIG. 5 is best suited for use in the back of the mouth, and comprises a second retention means 30 having two body segments 33 joined by a body joint angle 34, which may be formed as a curve or an angle joining linear segments. The body segments are shown as straight, but could also be curved. The delivery member 10 is attached to the attached end 32. To use the device, the dentist compresses the body joint 34 and inserts the device into the mouth so that the delivery member 10 is properly positioned and adhered against the upper or lower mucosa. The free end 31 of the second retention means 30 is positioned against the opposing mucosa, and the biasing force created by flexing the body joint 34 maintains the delivery member 10 in place between the restricting interior cheek wall and the upper and lower alveolar bone regions.

FIG. 6 shows an embodiment which is configured best for use in the front of the mouth. In this design, the second retention means 30 contains a main body joint 34 between two major body segments 33 as well as two minor body joints 34 connecting to two minor body segments 33, one having a free end 31 and the other having an attached end 32 to which is affixed the anesthetic delivery member 10. After compressing the body joint 34, the dentist positions the delivery member 10 at the desired location against the upper or lower mucosa and positions the free end 31 against the opposing mucosa. The two main body segments 33 and main body joint 34 may be allowed to protrude from the mouth between the lips, or they may be rotated and positioned between the cheek and teeth or between the tongue and palate. As before, the biasing force maintains the delivery member 10 in proper position even if the adhesion fails or weakens. FIG. 7 shows a similar embodiment to FIG. 6, the main body joint 34 shown as an angle rather than as a curve, with the delivery member 10 mounted generally perpendicularly to the minor segment 35. This configuration, again best suited for use in the front of the mouth, provides a better contact area between the delivery member 10 and the mucosa.

It is understood that equivalents and substitutions for components defined above may be obvious to those skilled in the art, and the true scope and definition of the invention therefore is to be as set forth in the following claims.

I claim:

1. A device for applying topical anesthetic to mucosal tissue in the mouth, the device comprising a delivery member which receives anesthetic and delivers said anesthetic to mucosal tissue, a first retention means comprising an adhesive which adheres said delivery member to said mucosal tissue, and a second retention means connected to said delivery member and composed of a generally rigid and flexible material, said second retention means applying a biasing force against said delivery member which secures said delivery member in position when said device is placed in a mouth, said biasing force being sustained by contact between said second retention member and anatomical structures of the mouth.

2. The device of claim 1, where said delivery member comprises a spun cotton material.

3. The device of claim 1, where said delivery member comprises a polymer foam.

4. The device of claim 1, where said delivery member comprises a woven material.

5. The device of claim 1, where said delivery member comprises a polymer matrix.

6. The device of claim 1, where said first retention means comprises an adhesive incorporated into said delivery member.

7. The device of claim 1, where said first retention means comprises an adhesive film adhered to said delivery member.

8. The device of claim 1, where said first retention means comprises an adhesive layer applied to said delivery member.

9. The device of claim 1, where said second retention means is generally elongated and thin.

10. The device of claim 1, where said second retention means is straight.

11. The device of claim 1, where said second retention means is curved.

12. The device of claim 1, where said second retention means comprises a body joint.

13. The device of claim 1, where said second retention means is malleable, such that said second retention means can be shaped into a desired configuration.

14. The device of claim 1, where said second retention means has an attached end, and said delivery member is connected to said attached end.

15. The device of claim 1, where said second retention means has two free ends, and said delivery member is connected to said second retention means between said two free ends.

16. An applicator device for applying a substance to tissue in the mouth, the device comprising a delivery member, a first retention means comprising an adhesive which adheres said delivery member to mouth tissue, and a second retention means connected to said delivery member and composed of a generally rigid and flexible material, said second retention means applying a biasing force against said delivery member which secures said delivery member in position when said device is placed in a mouth, the biasing force being sustained by contact between said second retention means and anatomical features of the mouth.

17. A method of applying topical anesthetic to the mucosal tissue of a mouth, the method comprising providing a device comprising a delivery member which receives anesthetic and delivers said anesthetic to mucosal tissue, a first retention means comprising an adhesive which adheres said delivery member to said mucosal tissue, and a second retention means connected to said delivery member and composed of a generally rigid and flexible material, said second retention means applying a biasing force against said delivery member which secures said delivery member in position when said device is placed in a mouth, compressing said second retention means to create a biasing force, inserting said device into a mouth such that said delivery member contacts the mucosal tissue at a desired location, adhering said delivery member to the mucosal tissue, positioning said second retention means to contact anatomical structures of the mouth such that the anatomical features sustain the biasing force against said delivery member, and releasing said second retention means.

* * * * *